US008926900B2

(12) United States Patent
Elders et al.

(10) Patent No.: US 8,926,900 B2
(45) Date of Patent: Jan. 6, 2015

(54) THERMAL CONDUCTIVITY DETECTION METHOD AND DEVICE FOR GAS CHROMATOGRAPHY

(75) Inventors: Job Elders, Hengelo Ov (NL); Gert-Jan Burger, Hengelo Ov (NL)

(73) Assignee: Thermo Fisher Scientific S.p.A., Rodano (IT)

( * ) Notice: Subject to any disclaimer, the term of this patent is extended or adjusted under 35 U.S.C. 154(b) by 285 days.

(21) Appl. No.: 12/999,390

(22) PCT Filed: Jun. 10, 2009

(86) PCT No.: PCT/NL2009/000130
§ 371 (c)(1),
(2), (4) Date: Dec. 16, 2010

(87) PCT Pub. No.: WO2009/154442
PCT Pub. Date: Dec. 23, 2009

(65) Prior Publication Data
US 2011/0091983 A1  Apr. 21, 2011

(30) Foreign Application Priority Data
Jun. 17, 2008 (NL) .................................. 1035591

(51) Int. Cl.
*G01N 27/00* (2006.01)
*G01N 30/66* (2006.01)
*G01N 30/78* (2006.01)

(52) U.S. Cl.
CPC ................ *G01N 30/66* (2013.01); *G01N 30/78* (2013.01)

USPC ............... 422/54; 436/154; 436/149; 73/23.4

(58) Field of Classification Search
None
See application file for complete search history.

(56) References Cited

FOREIGN PATENT DOCUMENTS

WO    WO 2007/081416 A1    7/2007

OTHER PUBLICATIONS

Hsu, H.J. et al. Characterization of synthetic polymers by electrospray-assisted pyrolysis ionization-mass spectrometry, 2005, Analytical Chemistry, vol. 77(23), pp. 7744-7749.*

* cited by examiner

*Primary Examiner* — Robert Xu
(74) *Attorney, Agent, or Firm* — Charles B. Katz

(57) ABSTRACT

Improved system for gas chromatography wherein use is made of a separation column and a TCD (Thermal Conductivity Detector), characterized in that the outflow from the separation column is ionized, and the ionization takes place upstream of the TCD. The ionization of the outflow from the separation column upstream of the TCD is surprisingly found in many cases to have a favorable effect on the response of the TCD. The sensitivity of the TCD is found in many cases to increase substantially. For ionization purposes use can be made of electromagnetic radiation, ionizing radiation or pyrolysis. The degree of ionization is preferably measured by means of measuring means provided for the purpose. The response of the TCD and the measurement data obtained with the measuring means are found together to give in many cases even more and better information relating to components present in the outflow from the separation column.

8 Claims, 1 Drawing Sheet

THERMAL CONDUCTIVITY DETECTION METHOD AND DEVICE FOR GAS CHROMATOGRAPHY

FIELD OF THE INVENTION

The invention relates to an improved method for gas chromatography, wherein use is made of a separation column and a TCD (Thermal Conductivity Detector). The invention also relates to an improved device for gas chromatography, comprising a separation column and a TCD. The object here is to influence or improve the response of the TCD.

BACKGROUND OF THE INVENTION

Chromatography is one of the oldest chemical analysis methods in which a mixture is separated into individual chemical components. It thus becomes simpler to make a qualitative or quantitative determination of the chemical components in a mixture. In gas chromatography the mixture is guided through a separation column by means of an inert carrier gas: the mobile phase, usually helium or hydrogen. The separation is based on the differential interactions between the different chemical components in the mobile phase and an immobilized stationary phase: a liquid or solid material with which the inner wall of the separation column is covered or which is arranged on an inert carrier material in the separation column. The retention time of a chemical component in the separation column is a function of the measure of interaction with the stationary phase, the type and the quantity of stationary phase, the length and diameter of the separation column, the type of carrier gas, the flow speed and the temperature. The different chemical components will in principle now leave the separation column at different points in time. These points in time can be determined by guiding the outflow from the separation column to a detector. The different chemical components then appear as more or less sharp 'peaks' in the output of the detector: the chromatogram.

A TCD (Thermal Conductivity Detector) is usually used as detector in gas chromatography. Changes in the thermal conductivity of the outflow from the separation column can be detected herewith. This conductivity is compared to the conductivity of the pure carrier gas. Because most substances have a conductivity which is much lower than that of the carrier gas used, the conductivity is decreased when a component passes through, and this produces a difference signal. The TCD comprises a temperature-dependent electrical resistor placed in a detector body with a constant temperature. The outflow from the separation column is guided along the resistor. When there is a constant electric current through the resistor, there is normally speaking a stable heat flow from the resistor to the detector body. When a component passes through, the thermal conductivity of the gas enclosing the resistor drops. The resistor is then less well able to relinquish its heat and heats up. Because the electrical resistance of the resistor is temperature-dependent, it will therefore also change. This change is usually measured using a wheatstone bridge. Because practically all components, organic or inorganic, have a thermal resistance substantially different from the carrier gas, practically all components in the outflow can be detected by means of a TCD. The TCD is therefore a more or less universal detector.

In addition to a non-destructive TCD, other types of destructive detectors can also be utilized, such as an FID (Flame Ionization Detector), a PID (Photo Ionization Detector) an ECD (Electron Capture Detector) and an MDD (Micro Discharge Detector), these detectors being more sensitive to specific groups of components, see for instance WO 2007/081416 A1. The detectors in which ionization takes place are placed after, i.e. downstream of, the TCD and the ionization thus takes place downstream of the TCD.

In addition to being determined by the properties of the separation column, the injector and the carrier gas and the measure of control of sample injection, gas flows, pressures, temperatures and so on, the quality of a system for gas chromatography is particularly also determined by the properties of the detector or detectors. The sensitivity, accuracy and precision of the detector or detectors are preferably as high as possible. The invention now provides a solution for the purpose of influencing or improving the response of a TCD.

SUMMARY OF THE INVENTION

The invention provides an improved system for gas chromatography wherein use is made of a separation column and a TCD (Thermal Conductivity Detector), characterized in that the outflow from the separation column is ionized. In the context of the invention 'outflow' is understood to mean the flow of carrier gas and components between the separation column and the TCD. In the extreme cases the ionization can take place in or at the end of the separation column or at the entry of or inside the TCD. The ionization thus takes place according to the invention upstream of the TCD or, in the extreme case, inside the TCD. In this latter case the ionization means can be integrated with the TCD, this resulting in functional advantages and advantages in respect of production engineering. The ionization of the outflow from the separation column upstream of the TCD is surprisingly found in many cases to have a favourable effect on the response of the TCD. The sensitivity of the TCD is found in many cases to increase substantially. It is noted for the sake of clarity that what is involved here is the measurement of thermal conductivity as described above, and not the measurement of an ionization current or electron current such as in an FID, PID, ECD or MDD. The chemistry and physics behind the phenomenon of changing the response of a TCD are not yet well understood. The present applicant is doing further research into this.

For ionization purposes use can be made of electromagnetic radiation, preferably ultraviolet light. Suitable ultraviolet lamps are readily obtainable and are already widely applied in ECDs (Electron Capture Detectors). A source of ultraviolet light can however also be developed and manufactured specially for this purpose, optionally integrated to greater or lesser extent with the device or the TCD.

Use can also be made of ionizing radiation, preferably beta radiation. Radioactive $^{63}$Ni can for instance be used as source for this purpose, this material already being widely used in ECDs. Americium is however preferably used as source. Americium is relatively weakly radioactive and is not therefore subject, as $^{63}$Ni, to all kinds of strict rules and regulations. Particularly in a microtechnological device or TCD, the americium can be arranged sufficiently close to the outflow so that, despite its weaker radioactivity, sufficient ionization nevertheless takes place. The radioactive source can here once again optionally be integrated to greater or lesser extent with the device or the TCD.

Use can in principle also be made of pyrolysis for the purpose of ionization, preferably using a flame. Ionization by means of a flame is known from an FID. Here too the ionization means can in principle again optionally be integrated to greater or lesser extent with the device or the TCD, although this will be much less simple in the case of a flame. Pyrolysis is moreover destructive and therefore less suitable in many cases.

The degree of ionization is preferably also measured by means of measuring means provided for the purpose. The measuring means will generally comprise electrodes with which an ion current can be measured, such as in an FID, PID or ECD. The measuring means can be placed downstream of the TCD, in the extreme case inside the TCD, in which case the measuring means can again be integrated to greater or lesser extent with the TCD. The response of the TCD and the measurement data obtained with the measuring means are found together to give in many cases more and better information relating to components present in the outflow.

BRIEF DESCRIPTION OF THE FIGURES

The invention is elucidated hereinbelow on the basis of two non-limitative exemplary embodiments of a device according to the invention. Herein.

EXEMPLARY EMBODIMENTS OF A DEVICE ACCORDING TO THE INVENTION

Figure 1:
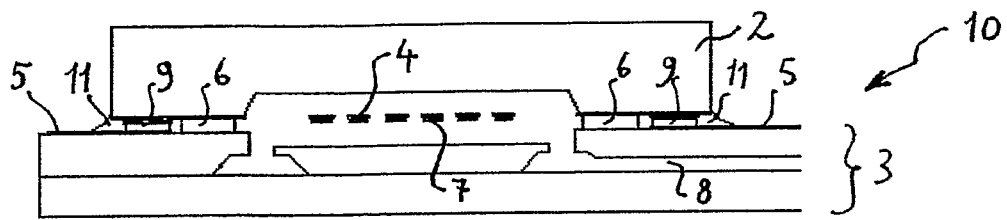
FIG. 1 shows a more or less schematic section of a known device comprising a TCD.

FIG. 1 shows a known device (10) manufactured with microtechnology developed by the present applicant. Device (10) comprises a chip (2) of silicon or glass, having for instance lateral dimensions of 3×5 mm$^2$, arranged on a channel plate (3) by means of flip-chip technology. Channel plate (3) is typically of silicon or glass, with for instance lateral dimensions of 20×30 mm$^2$, provided with a fluidic circuit (8) and an electrical circuit (5). Circuits (8,5) form the connection between chip (2) and an input or output of device (10) or one or more other structural parts arranged on channel plate (3). Typical dimensions of channels (8) are square 25 to 250 micrometers. An elastomer gasket (6), typically 100 micrometers thick, forms a seal between chip (2) and channel plate (3). Electrical connections are also made by means of electrical contacts (9) between electrical circuit (5) on channel plate (3) and an electrical resistor (7) arranged on a perforated membrane (4) forming part of chip (2). The whole thus forms with the required further electronics a TCD.

Figure 2:
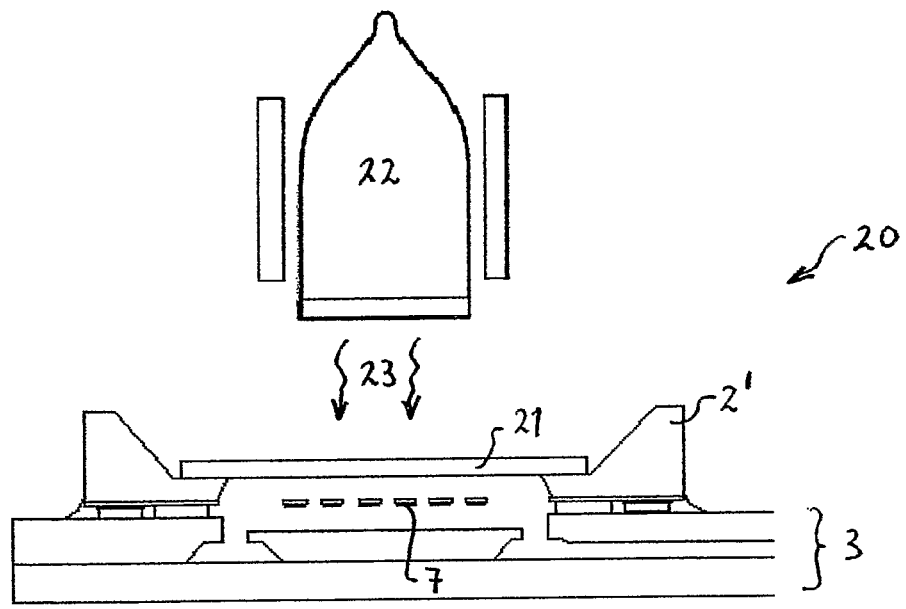
FIG. 2 shows a more or less schematic section of a first exemplary embodiment of a device according to the invention.

FIG. 2 shows a first exemplary embodiment of a device (20) according to the invention, starting from the known device (10) of FIG. 1. In chip (2') is now arranged a window (21) which is transparent to ultraviolet (UV) radiation, for instance of magnesium fluoride. Gas flowing along resistor (7) can be ionized by means of UV radiation (23) from a UV lamp (22) provided for the purpose. The ionization is now found in many cases to have a favourable effect on the response of the TCD. The sensitivity of the TCD is found in many cases to be substantially greater than in the known device (10). What is involved here is the measurement of thermal conductivity, and not the measurement of an ionization current or electron current.

Figure 3:
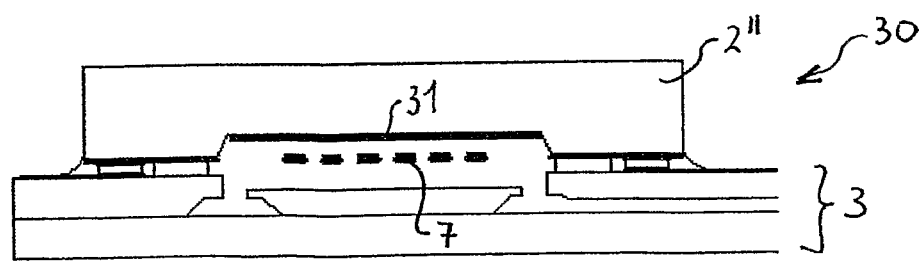
FIG. 3 shows a more or less schematic section of a second exemplary embodiment of a device according to the invention.

FIG. 3 shows a second exemplary embodiment of a device (30) according to the invention, starting from the known device (10) of FIG. 1. In chip (2") is now arranged a radioactive layer (31), in this example of americium. Gas flowing along resistor (7) is ionized by means of the ionizing radiation from radioactive layer (31). The ionization is once again found in many cases to have a favourable effect on the response of the TCD.

A device according to the invention can also comprise electrodes with which an ion current can be measured. The electrodes can be placed downstream of the TCD or inside the TCD. In the latter case the electrodes can be integrated relatively simply with the TCD. The response of the TCD and the measured ion current are together found to give even more and better information relating to the components present in the outflow.

The chemistry and physics behind this phenomenon of the change in the response of a TCD due to the ionization of the outflow from a separation column upstream of the TCD are not yet well understood. The present applicant is carrying out further research into this.

It will be apparent that the invention is not limited to the given exemplary embodiments, but that diverse variants are possible within the scope of the invention.

The invention claimed is:

1. A gas chromatography device, comprising:
   a separation column;
   ionization means for ionizing the outflow from the separation column; and
   a thermal conductivity detector (TCD) for detecting components in the ionized outflow,
   wherein the ionization means are situated upstream of or inside the TCD.

2. The device of claim 1, wherein the ionization means are situated inside the TCD.

3. The device of claim 1, wherein the ionization means comprise means for producing electromagnetic radiation.

4. The device of claim 1, wherein the ionization means comprise means for producing ionizing radiation.

5. The device of claim 4, wherein the means for producing ionizing radiation comprise americium.

6. The device of claim 1, wherein the ionization means comprise pyrolysis means.

7. The device of claim 1, further comprising measuring means for measuring a degree of ionization.

8. The device of claim 1, wherein the ionization means are situated upstream of the TCD.

* * * * *